United States Patent
Schiff et al.

(10) Patent No.: US 10,456,300 B2
(45) Date of Patent: Oct. 29, 2019

(54) RING COMPRESSION BANDAGE

(71) Applicants: Benjamin Schiff, Dunwoody, GA (US); Don Schiff, Dunwoody, GA (US)

(72) Inventors: Benjamin Schiff, Dunwoody, GA (US); Don Schiff, Dunwoody, GA (US)

(*) Notice: Subject to any disclaimer, the term of this patent is extended or adjusted under 35 U.S.C. 154(b) by 752 days.

(21) Appl. No.: 14/560,881

(22) Filed: Dec. 4, 2014

(65) Prior Publication Data
US 2016/0158065 A1 Jun. 9, 2016

(51) Int. Cl.
*A61F 13/00* (2006.01)
(52) U.S. Cl.
CPC .. *A61F 13/00021* (2013.01); *A61F 13/00012* (2013.01); *A61F 13/00017* (2013.01); *A61F 2013/00106* (2013.01)
(58) Field of Classification Search
CPC ............... A61F 13/00; A61F 13/00021; A61F 13/00017; A61F 13/00012; A61F 2013/00106; A61F 13/12; A61F 2013/00468; A61L 15/04; A61L 15/42; A61L 15/24
See application file for complete search history.

(56) References Cited

U.S. PATENT DOCUMENTS

| | | | |
|---|---|---|---|
| 3,157,178 A | 11/1964 | Bentov | |
| 3,490,448 A | 1/1970 | Grubb | |
| 3,561,442 A | 2/1971 | Goswitz | |
| 4,005,709 A * | 2/1977 | Laerdal | A61F 13/00021 602/53 |
| 4,345,591 A | 8/1982 | Hedgren | |

(Continued)

FOREIGN PATENT DOCUMENTS

WO WO 2012168824 A1 * 12/2012 ............. A61F 13/00

OTHER PUBLICATIONS

Access Health, http://www.accesshealth.com.au/practice-supplies/compressionbandages/3703/esmarch-tourniquet-bandagering-sterile/, Esmarch Tourniquet Bandage/Ring Sterile, found online Sep. 30, 2014.

(Continued)

*Primary Examiner* — Tatyana Zalukaeva
*Assistant Examiner* — Sara A Sass
(74) *Attorney, Agent, or Firm* — Crose Law LLC; Bradley D. Crose

(57) ABSTRACT

A toroidal compression bandage includes: a soft fibrous material, defined by an absorbency of a predetermined amount; a compression bandage form comprised of soft fibrous absorbent material in a rolled, wrapped form and of a shape defined by a circle revolved in three-dimensional space about a circular axis coplanar with the circle, wherein the axis of revolution does not touch the rotated circle, to define a torus ring compression bandage; an aperture defined within a center area of the torus ring compression bandage as it is formed, the aperture having a predetermined diameter and configured for placement directly over a trauma wound to avoid contact with the trauma wound; and a compression surface defined on an underside of the torus ring compression bandage, the compression surface configured for circumferential placement around the trauma wound to avoid direct contact of the trauma wound, and for absorption placement around the trauma wound.

20 Claims, 16 Drawing Sheets

(56) References Cited

U.S. PATENT DOCUMENTS

| | | | |
|---|---|---|---|
| 4,377,159 A | 3/1983 | Hansen | |
| 4,981,133 A | 1/1991 | Rollband | |
| 5,031,609 A | 7/1991 | Fye | |
| 5,264,218 A | 11/1993 | Rogozinski | |
| 5,356,372 A | 10/1994 | Donovan et al. | |
| 5,376,067 A | 12/1994 | Daneshvar | |
| 5,628,723 A | 5/1997 | Grau | |
| 5,665,060 A * | 9/1997 | Fabricant | A61F 5/019 128/893 |
| 5,891,074 A | 4/1999 | Cesarczyk | |
| 6,071,268 A * | 6/2000 | Wagner | A61F 5/443 604/332 |
| 6,441,265 B1 * | 8/2002 | Chan | A61F 13/0203 602/41 |
| 6,762,337 B2 | 7/2004 | Boukanov | |
| 7,479,577 B2 * | 1/2009 | Scheinberg | A61F 13/06 128/882 |
| 7,854,716 B2 | 12/2010 | Schuren | |
| 8,262,601 B2 | 11/2012 | Cumming et al. | |
| 8,415,523 B2 | 4/2013 | Aali et al. | |
| 8,562,553 B2 | 10/2013 | Naumann | |
| 8,586,818 B2 | 11/2013 | Aali | |
| D705,428 S | 5/2014 | Cheney et al. | |
| D705,429 S | 5/2014 | Cheney et al. | |
| 8,790,154 B2 | 7/2014 | Blackwell | |
| 2005/0004500 A1 * | 1/2005 | Rosser | A61B 5/447 602/41 |
| 2005/0165445 A1 * | 7/2005 | Buckman | A61F 13/00 606/213 |
| 2009/0306570 A1 | 12/2009 | Bauerfeind | |
| 2010/0016775 A1 | 1/2010 | Cumming et al. | |
| 2011/0288509 A1 | 11/2011 | Bar-Natan et al. | |
| 2012/0296252 A1 | 11/2012 | Cumming et al. | |
| 2013/0310809 A1 * | 11/2013 | Armstrong | A61M 1/0088 604/543 |
| 2014/0012174 A1 * | 1/2014 | Wu | A61F 13/0223 602/53 |
| 2014/0121627 A1 * | 5/2014 | Lepore | A61F 13/00 604/385.01 |

OTHER PUBLICATIONS

Bandaging, The Ring Bandage, found online Sep. 30, 2014, at https://www.youtube.com/watch?v=-QspPN2hnRQ.

* cited by examiner

RING COMPRESSION BANDAGE

FIELD OF THE INVENTION

The technology described herein relates generally to medical compression bandages, pressure bandages, and wound dressings. More specifically, this technology relates to a ring compression bandage useful, for example, for first aid on head injuries with a compromised skull causing brain matter to be exposed, or a penetration injury with an object sticking out of the body requiring a bandage that goes around the penetrating object to provide compression in order to reduce bleeding.

BACKGROUND OF THE INVENTION

Bandages, medical compression bandages, pressure bandages, and wound dressings are useful in the treatment of injuries, protection of exposed wounds, prevention of blood loss, and so forth. Deficiencies and limitations exist with the bandages, medical compression bandages, pressure bandages, and wound dressings known in the background art.

Related utility patents known in the art include the following:

U.S. Pat. No. 3,157,178, issued to Bentov on Nov. 17, 1964, discloses a dressing.

U.S. Pat. No. 3,490,448, issued to Grubb on Jul. 31, 1967, discloses an adhesive pressure pad.

U.S. Pat. No. 3,561,442, issued to Goswitz on Feb. 9, 1971, discloses a mastectomy compression bandage.

U.S. Pat. No. 4,981,133, issued to Rollband on Jan. 1, 1991, discloses a pressure bandage for puncture wounds with a target marking.

U.S. Pat. No. 5,031,609, issued to Fye on Jul. 16, 1991, discloses a postoperative compression bandage for the head.

U.S. Pat. No. 5,264,218, issued to Rogozinski on Nov. 23, 1993, discloses a modifiable, semi-permeable would dressing.

U.S. Pat. No. 5,376,067, issued to Daneshvar on Dec. 27, 1994, discloses pressure bandages and dressings.

U.S. Pat. No. 6,441,265, issued to Chan on Aug. 27, 2002, discloses a wound dressing.

U.S. Pat. No. 6,762,337, issued to Boukanov et al. on Jul. 13, 2004, discloses pressure bandages for wounds.

U.S. Pat. No. 7,854,716, issued to Schuren et al. on Dec. 21, 2010, discloses a compression bandage system.

U.S. Pat. No. 8,262,601, issued to Cumming et al. on Sep. 11, 2012, discloses a helmet trauma bandage and method.

U.S. Pat. No. 8,562,553, issued to Naumann on Oct. 22, 2013, discloses a compression bandage.

U.S. Pat. No. 8,586,818, issued to Aali on Nov. 19, 2013, discloses a wound shield.

U.S. Pat. No. 8,790,154, issued to Blackwell on Jul. 29, 2014, discloses a post-operative compression bra.

U.S. Pat. No. 4,005,709, issued to Laerdal on Feb. 1, 1977, discloses a compression bandage.

U.S. Pat. No. 4,345,591, issued to Hedgren on Aug. 24, 1982, discloses a mound dressing.

U.S. Pat. No. 4,377,159, issued to Hansen on Mar. 22, 1983, discloses pressure bandages and methods for making the same.

U.S. Pat. No. 5,356,372, issued to Donovan et al. on Oct. 18, 1994, discloses an occlusive pressure-reducing wound dressing.

U.S. Pat. No. 5,891,074, issued to Cesarczyk on Apr. 6, 1999, discloses a pressure wound dressing.

U.S. Pat. No. 8,415,523, issued to Aali et al. on Apr. 9, 2013, discloses secondary wound dressing for securing primary dressings and managing fluid from wounds, and methods of using the same.

U.S. Pat. No. 5,628,723, issued to Grau on May 13, 1997, discloses an emergency bandage.

Related utility patent application publications known in the art include the following:

U.S. Patent Application Publication No. 2009/0306570, filed by Bauerfeind and published on Dec. 10, 2009, discloses a tubular compression bandage.

U.S. Patent Application Publication No. 2010/0016775, filed by Cumming et al. and published on Jan. 21, 2010, discloses a head trauma bandage and method.

U.S. Patent Application Publication No. 2012/0296252, filed by Cumming et al. and published on Nov. 22, 2012, discloses head trauma bandage cap and method.

U.S. Patent Application Publication No. 2011/0288509, filed by Bar-Natan et al. and published on Nov. 24, 2011, discloses a multi-bandage.

Related design patents known in the art include the following:

U.S. Pat. No. D 705,428, issued to Cheney et al. on May 20, 2014, discloses a medical compression bandage.

U.S. Pat. No. D 705,429, issued to Cheney et al. on May 20, 2014, discloses a medical compression bandage.

Related non-patent literature known in the art includes the following:

The Esmarch tourniquet bandage and ring. This product is provided by Access Health and found online at http://www.accesshealth.com.au/practice-supplies/compression-bandages/3703/esmarch-tourniquet-bandagering-sterile/.

The ring bandage. This reference is found online at https://www.youtube.com/watch?v=-QspPN2hnRQ.

The foregoing patent and other information reflect the state of the art of which the inventor is aware and are tendered with a view toward discharging the inventor's acknowledged duty of candor in disclosing information that may be pertinent to the patentability of the technology described herein. It is respectfully stipulated, however, that the foregoing patent and other information do not teach or render obvious, singly or when considered in combination, the inventor's claimed invention.

BRIEF SUMMARY OF THE INVENTION

In various exemplary embodiments, the technology described herein provides a ring compression bandage useful, for example, for first aid on head injuries with a compromised skull causing brain matter to be exposed, or a penetration injury with an object sticking out of the body requiring a bandage that goes around the penetrating object to provide compression in order to reduce bleeding.

In one exemplary embodiment, the technology described herein provides a toroidal In one exemplary embodiment, the technology described herein provides a toroidal compression bandage. The toroidal compression bandage includes: a soft fibrous material, defined by an absorbency of a predetermined amount; a compression bandage form comprised of the soft fibrous absorbent material in a rolled, wrapped form and of a shape defined by a circle revolved in three-dimensional space about a circular axis coplanar with the circle, wherein the axis of revolution does not touch the rotated circle, thereby to define a torus ring compression bandage; an aperture defined within a center area of the torus ring compression bandage as it is formed, the aperture having a predetermined diameter and configured for placement directly over a trauma wound to avoid direct contact with the trauma wound; and a compression surface defined on an underside of the torus ring compression bandage, the compression surface configured for circumferential placement around the trauma wound to avoid direct contact of the trauma wound, and for absorption placement around the trauma wound.

In at least one embodiment, the toroidal compression bandage further includes an outer encasement defined in a torus ring shape as the torus ring compression bandage and configured to surround and encase the torus ring compression bandage and to contain the soft fibrous material and compression bandage form.

In at least one embodiment of the toroidal compression bandage, the outer encasement is cotton netting.

In at least one embodiment of the toroidal compression bandage, the soft fibrous material, defined by an absorbency of a predetermined amount is gauze.

In at least one embodiment of the toroidal compression bandage, the soft fibrous material, defined by an absorbency of a predetermined amount is cotton.

In at least one embodiment of the toroidal compression bandage further includes a core of tubular shape, configured to resist compression. The compression bandage form comprised of the soft fibrous absorbent material in a rolled, wrapped form is rolled, wrapped around the core of tubular shape.

In at least one embodiment of the toroidal compression bandage, the core of tubular shape is hollow and the toroidal compression bandage further comprises supplemental soft fibrous material disposed within the hollow core of tubular shape.

In at least one embodiment of the toroidal compression bandage, the core of tubular shape is solid.

In at least one embodiment of the toroidal compression bandage, the core of tubular shape is foam.

In at least one embodiment of the toroidal compression bandage, the core of tubular shape comprises a weaved nylon tube. In at least one alternative embodiment the tubular shape comprises a weaved cotton tube.

In at least one embodiment of the toroidal compression bandage, the core of tubular shape is a porous nylon tube.

In at least one embodiment, the toroidal compression bandage further includes a first non-adhesive pad disposed on an underside surface of the toroidal compression bandage.

In at least one embodiment, the toroidal compression bandage further includes a second non-adhesive pad disposed on a topside surface of the toroidal compression bandage.

In at least one embodiment, the toroidal compression bandage further includes a third non-adhesive pad configured for placement to cover over a topside surface of the toroidal compression bandage and the aperture defined within the center area of the torus ring compression bandage and removable.

In at least one embodiment, the toroidal compression bandage further includes an attached supplemental fabric coupled to a top surface of the toroidal compression bandage and extended on at least one end in one direction from the toroidal compression bandage, thereby to provide a means to wrap securely the toroidal compression bandage upon a wound area.

In at least one embodiment, the toroidal compression bandage further includes an attached supplemental fabric coupled to a top surface of the toroidal compression bandage and extended in two opposed directions on opposing ends of the toroidal compression bandage, thereby to provide a means to wrap securely the toroidal compression bandage upon a wound area.

In at least one embodiment, the toroidal compression bandage further includes a cleat plate disposed upon a top surface of the toroidal compression bandage and at least one cleat disposed upon the cleat plate and configured to receive an attached supplemental fabric or an unattached supplemental fabric to wrap securely the toroidal compression bandage upon a wound area.

In at least one embodiment, the toroidal compression bandage further includes a cleat plate disposed upon a top surface of the toroidal compression bandage and a pair of cleats disposed upon the cleat plate and configured to receive an attached supplemental fabric or an unattached supplemental fabric to wrap securely the toroidal compression bandage upon a wound area. The pair of cleats are disposed upon the cleat plate are parallel to a direction of the attached supplemental fabric or an unattached supplemental fabric.

In at least one embodiment, the toroidal compression bandage further includes a cleat plate disposed upon a top surface of the toroidal compression bandage and a pair of cleats disposed upon the cleat plate and configured to receive an attached supplemental fabric or an unattached supplemental fabric to wrap securely the toroidal compression bandage upon a wound area. The pair of cleats are disposed upon the cleat plate are perpendicular to a direction of the attached supplemental fabric or an unattached supplemental fabric.

In at least one embodiment, the toroidal compression bandage further includes an unattached supplemental fabric to provide a means to wrap securely the toroidal compression bandage around an object.

There has thus been outlined, rather broadly, the more important features of the technology in order that the detailed description thereof that follows may be better understood, and in order that the present contribution to the art may be better appreciated. There are additional features of the technology that will be described hereinafter and which will form the subject matter of the claims appended hereto. In this respect, before explaining at least one embodiment of the technology in detail, it is to be understood that the invention is not limited in its application to the details of construction and to the arrangements of the components set forth in the following description or illustrated in the drawings. The technology described herein is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the technology described herein.

Further objects and advantages of the technology described herein will be apparent from the following detailed description of a presently preferred embodiment which is illustrated schematically in the accompanying drawings.

BRIEF DESCRIPTION OF THE DRAWINGS

The technology described herein is illustrated with reference to the various drawings, in which like reference numbers denote like device components and/or method steps, respectively, and in which.

DETAILED DESCRIPTION OF THE INVENTION

Before describing the disclosed embodiments of this technology in detail, it is to be understood that the technology is not limited in its application to the details of the particular arrangement shown here since the technology described is capable of other embodiments. Also, the terminology used herein is for the purpose of description and not of limitation.

In various exemplary embodiments, the technology described herein provides a ring compression bandage useful, for example, for first aid on head injuries with a compromised skull causing brain matter to be exposed, or a penetration injury with an object sticking out of the body requiring a bandage that goes around the penetrating object to provide compression in order to reduce bleeding.

Referring now to the Figures, a toroidal compression bandage 10 is shown. The toroidal compression bandage 10 includes a soft fibrous material 16. By way of example, and in at least one embodiment, the soft fibrous material 16 is a gauze bandage material. In another embodiment the soft fibrous material 16 is cotton. In another embodiment the soft fibrous material 16 has a loose open weave pattern. Alternative fabric-like materials also can be utilized, provided such material can be made sterile and that such material is absorbent for the absorption of blood and other bodily fluids in and around a wound.

The fibrous material 16 is an absorbent material and is defined by an absorbency of a predetermined amount. One factor in determining which fibrous material 16 is selected for the toroidal compression bandage 10 is the amount of absorbency. Depending on the nature of use of the toroidal compression bandage 10, such as bodily location, type of wound to dress, and so forth, this can vary as needed.

The toroidal compression bandage 10 includes a compression bandage form comprised of the soft fibrous absorbent material 16 in a rolled, wrapped form and of a shape defined by a circle revolved in three-dimensional space about a circular axis coplanar with the circle. The axis of revolution does not touch the rotated circle, thereby to define a torus ring compression bandage 10. The shape is thus torus, or simply referred to as ring-shaped or doughnut-shaped.

The compression bandage form includes an aperture 14 defined within a center area of the torus ring compression bandage as it is formed. The aperture 14 has a predetermined diameter and is configured for placement directly over a trauma wound to avoid direct contact with the trauma wound.

The compression bandage form includes a compression surface defined on an underside of the torus ring compression bandage 10. The compression surface is configured for circumferential placement around the trauma wound to avoid direct contact of the trauma wound, and for absorption placement around the trauma wound.

Figure 1:
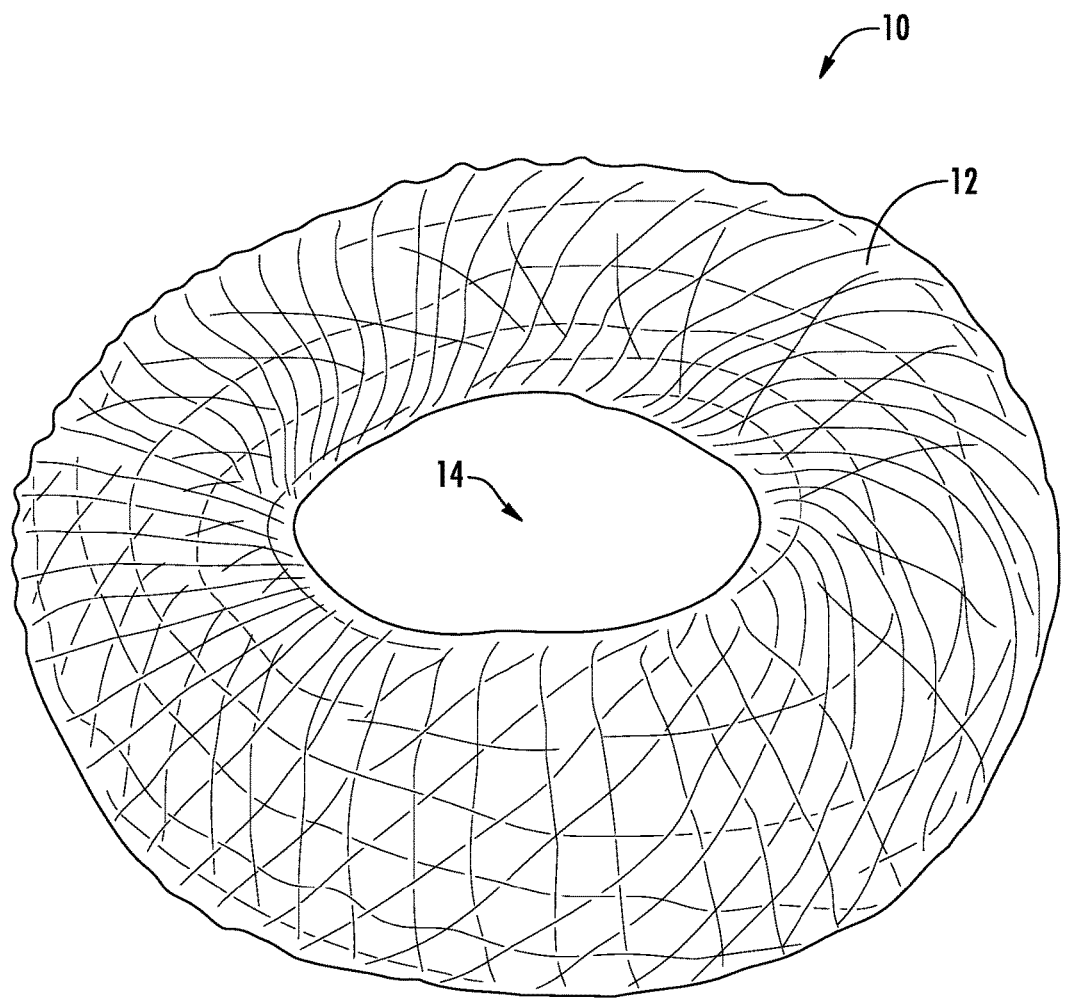
FIG. 1 is a front perspective view of a ring compression bandage, illustrating, in particular, an outer gauze layer, according to an embodiment of the technology described herein.
Figure 2:
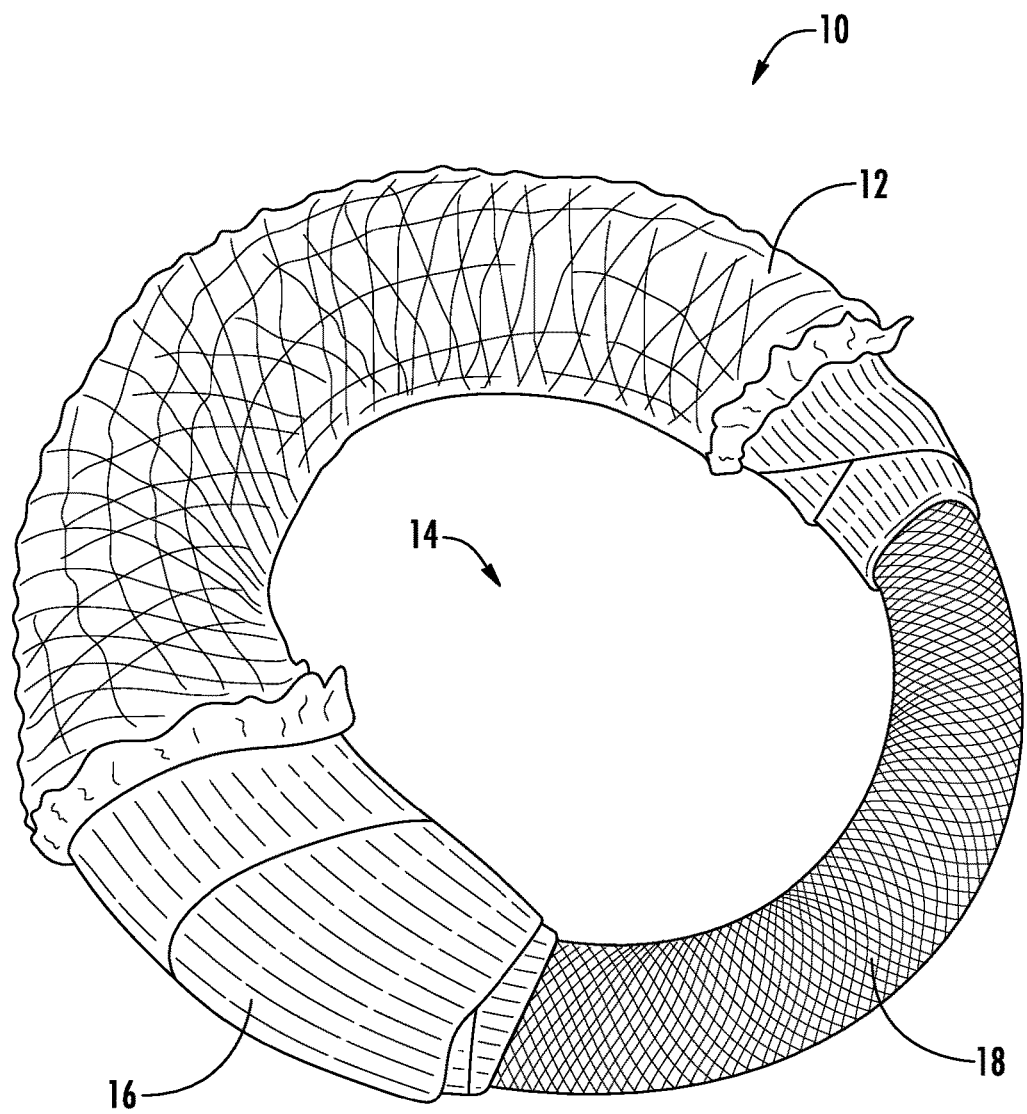
FIG. 2 is a front perspective, cut-away view of the ring compression bandage depicted in FIG. 1 illustrating, in particular, the tube, inner gauze, outer gauze, and aperture, according to an embodiment of the technology described herein.
Figure 3:
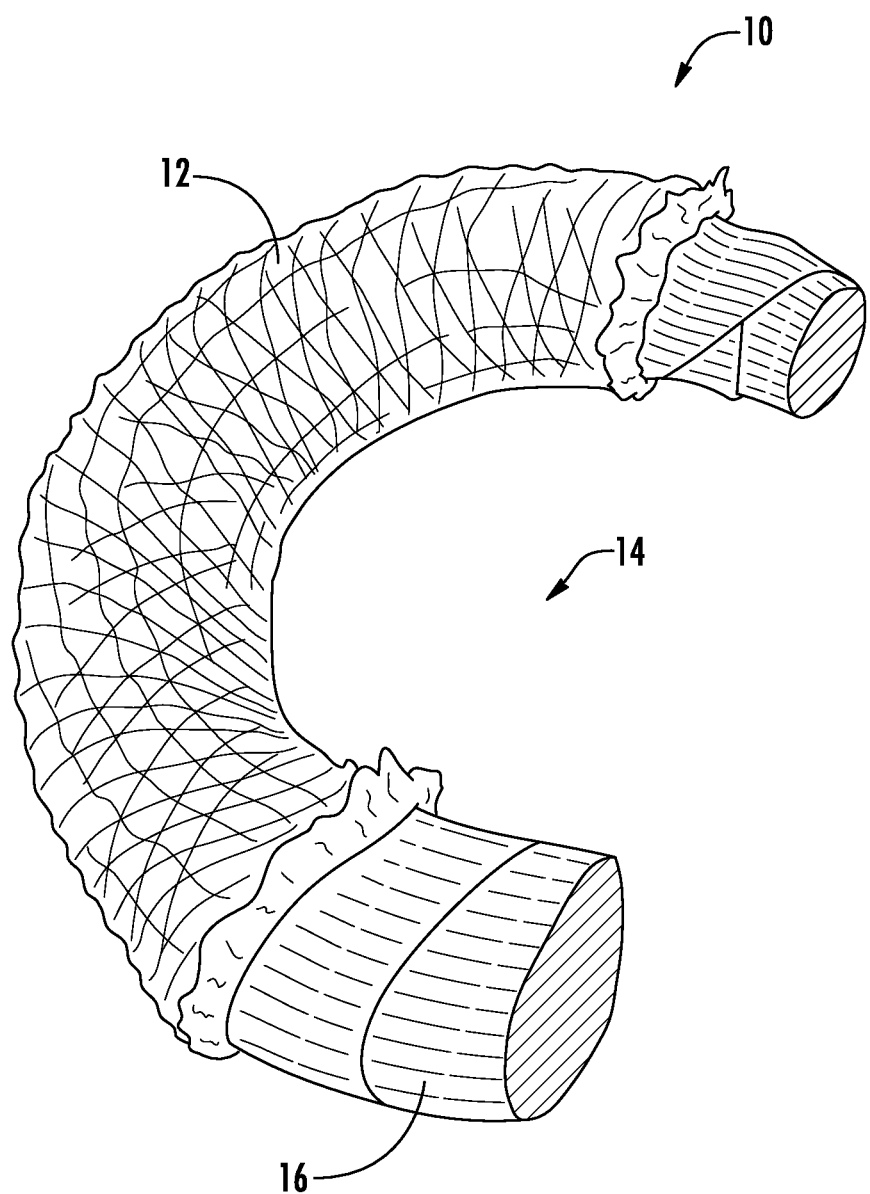
FIG. 3 is a front perspective, cross-sectional view of the ring compression bandage depicted in FIG. 1 illustrating, in particular, inner gauze, outer gauze, and aperture, yet not including a tube core, according to an embodiment of the technology described herein.

In at least one embodiment, the toroidal compression bandage 10 further includes an outer encasement 12. The outer encasement 12 is defined in a torus ring shape, the same as the torus ring compression bandage, and is configured to surround and encase the torus ring compression bandage and to contain the soft fibrous material 16 and compression bandage form. In at least one embodiment, the outer encasement 12 is cotton netting. FIGS. 1, 2, and 3 clearly depict the outer encasement 12.

In at least one embodiment, the toroidal compression bandage 10 further includes a core 18 of tubular shape. Alternatively, some embodiments of the toroidal compression bandage 10 do not include this core 18. The core 18 of tubular shape is configured to resist compression. The compression bandage form comprised of the soft fibrous absorbent material 16 in a rolled, wrapped form is rolled, wrapped around the core 18 of tubular shape.

FIG. 2 depicts the core 18 shown exposed on one portion and depicts the fibrous material 16 or gauze wrapped around the core 18. However, FIG. 3 depicts the fibrous material 16 or gauze wrapped within the toroidal compression bandage 10 but without use of a core 18.

In at least one embodiment of the toroidal compression bandage 10, the core 18 of tubular shape is solid.

In at least one embodiment of the toroidal compression bandage 10, the core 18 of tubular shape is foam.

In at least one embodiment of the toroidal compression bandage 10, the core 18 of tubular shape comprises a weaved nylon tube.

In at least one embodiment of the toroidal compression bandage 10, the core 18 of tubular shape is a porous nylon tube.

In at least one embodiment of the toroidal compression bandage 10, the core 18 of tubular shape is hollow. In this embodiment of the toroidal compression bandage 10, supplemental soft fibrous material 16 is disposed within the hollow core 18 of tubular shape.

In at least one embodiment, the toroidal compression bandage 10 further includes a first non-adhesive pad 20 disposed on an underside surface of the toroidal compression bandage 10. A stick-resistant bandage material is utilized for the first non-adhesive pad 20 and is attached to one side of the ring shaped article. The stick-resistant bandage material, the first non-adhesive pad 20, may be glued or sewn into the gauze fibrous material 16 or encasement 12. In at least one embodiment, the stick-resistant bandage material, the first non-adhesive pad 20, is sewn into a supplemental fabric.

Figure 4:
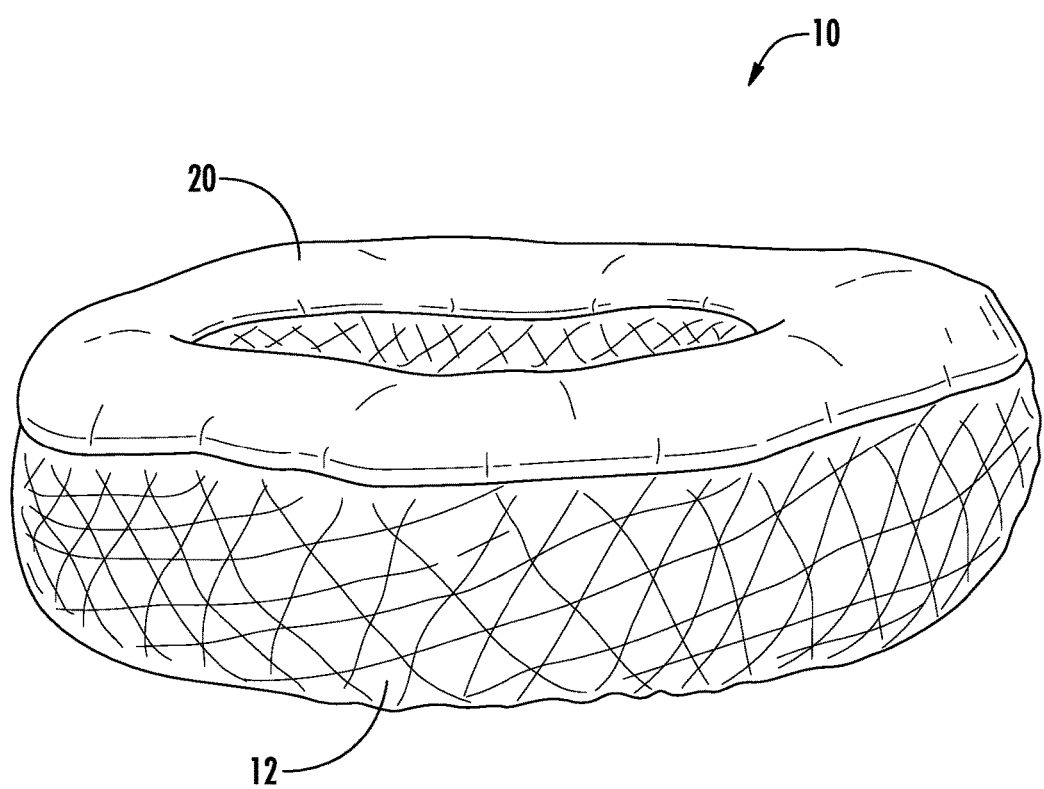
FIG. 4 is a perspective view of the ring compression bandage depicted in FIG. 1, illustrating, in particular, the addition of a non-adhesive layer to one side of the ring compression bandage, according to an embodiment of the technology described herein.
Figure 11:
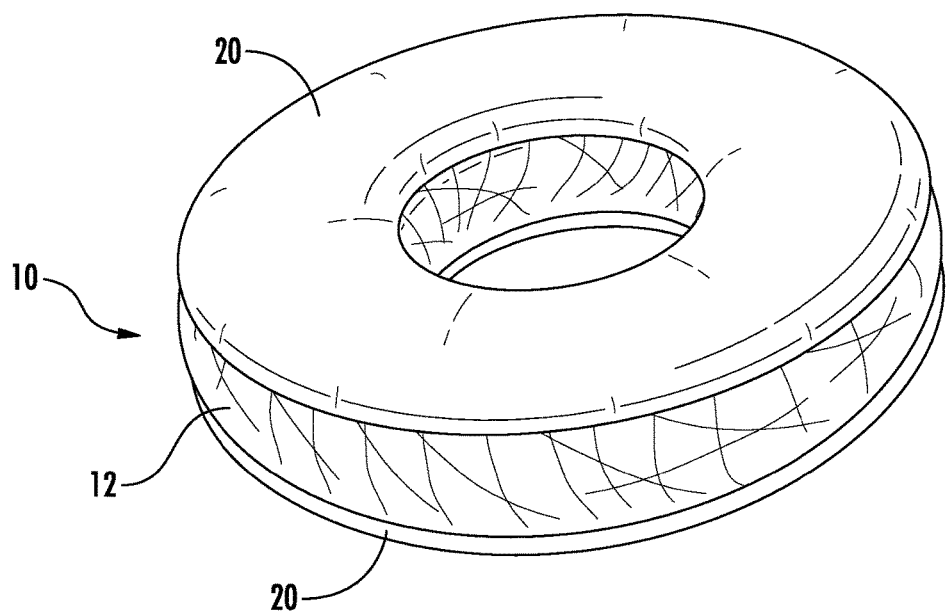
FIG. 11 is a perspective view of the ring compression bandage depicted in FIG. 1, illustrating, in particular, the addition of a non-adhesive layer to both side of the ring compression bandage, according to an embodiment of the technology described herein.
Figure 12:
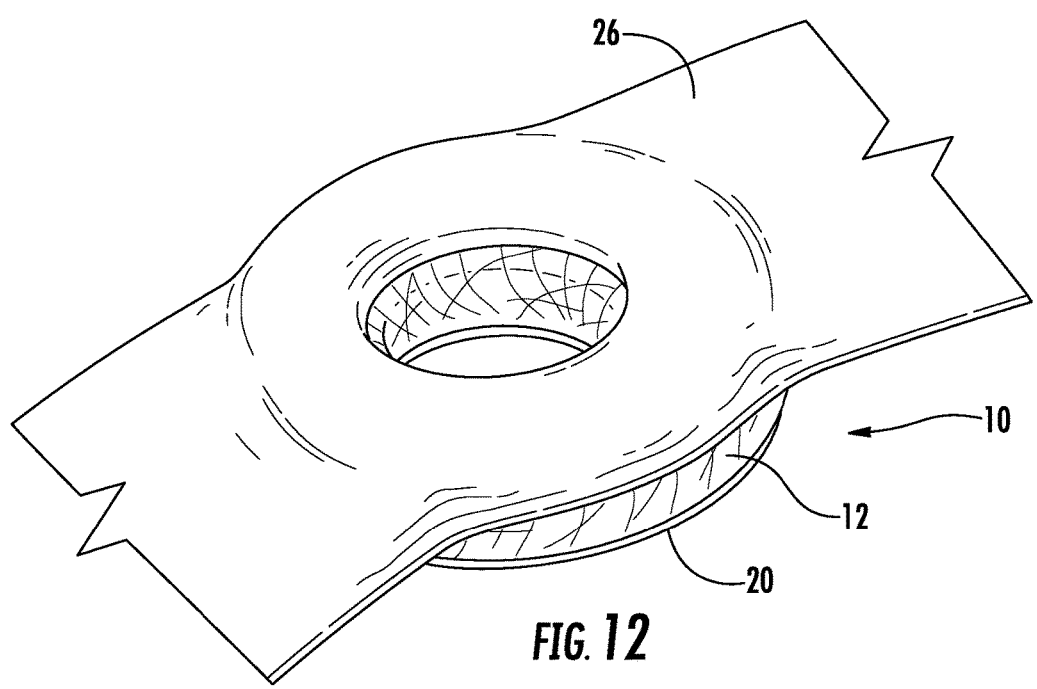
FIG. 12 is a perspective view of the ring compression bandage depicted in FIG. 11, illustrating, in particular, the ring compression bandage coupled to an elastic bandage, according to an embodiment of the technology described herein.
Figure 13:
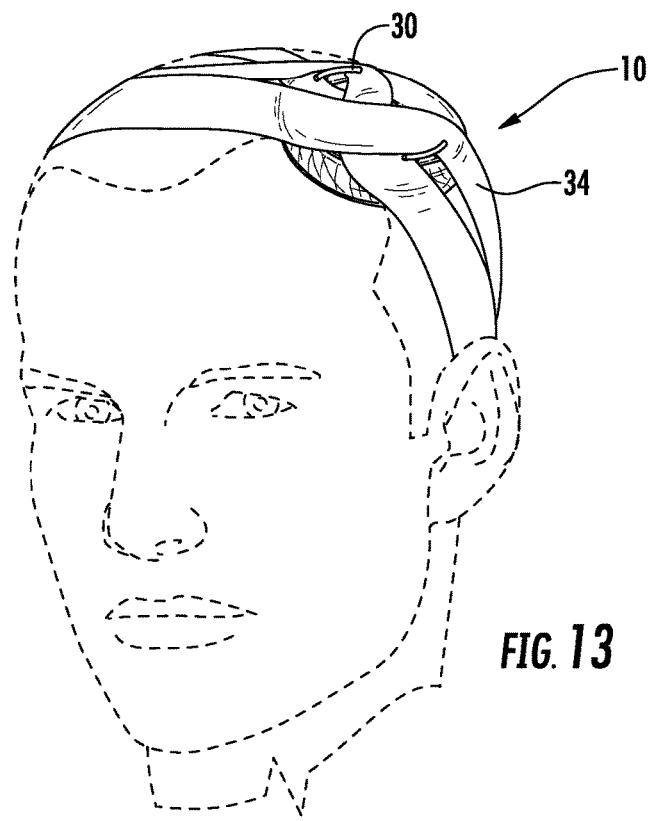
FIG. 13 is a perspective view of the ring compression bandage depicted in use for a person having a traumatic head injury, illustrating, in particular, the ring compression bandage having cleats and using a separate bandage to wrap the ring compression bandage, according to an embodiment of the technology described herein.

In at least one embodiment, the toroidal compression bandage 10 further includes a second non-adhesive pad 20 disposed on a topside surface of the toroidal compression bandage. The second non-adhesive pad 20 disposed on a topside surface is depicted in FIG. 4. In at least one embodiment, a non-adhesive pad 20 is utilized on both a top surface and an underside surface of the toroidal compression bandage 10. This is depicted in FIG. 11, for example.

In at least one embodiment, the toroidal compression bandage 10 further includes a third non-adhesive pad configured for placement to cover over a topside surface of the toroidal compression bandage and the aperture 14 defined within the center area of the torus ring compression bandage and removable. This version of the non-adhesive pad as a cover is not shown, but would be the same as already depicted but would additionally cover the aperture 14.

Figure 8:
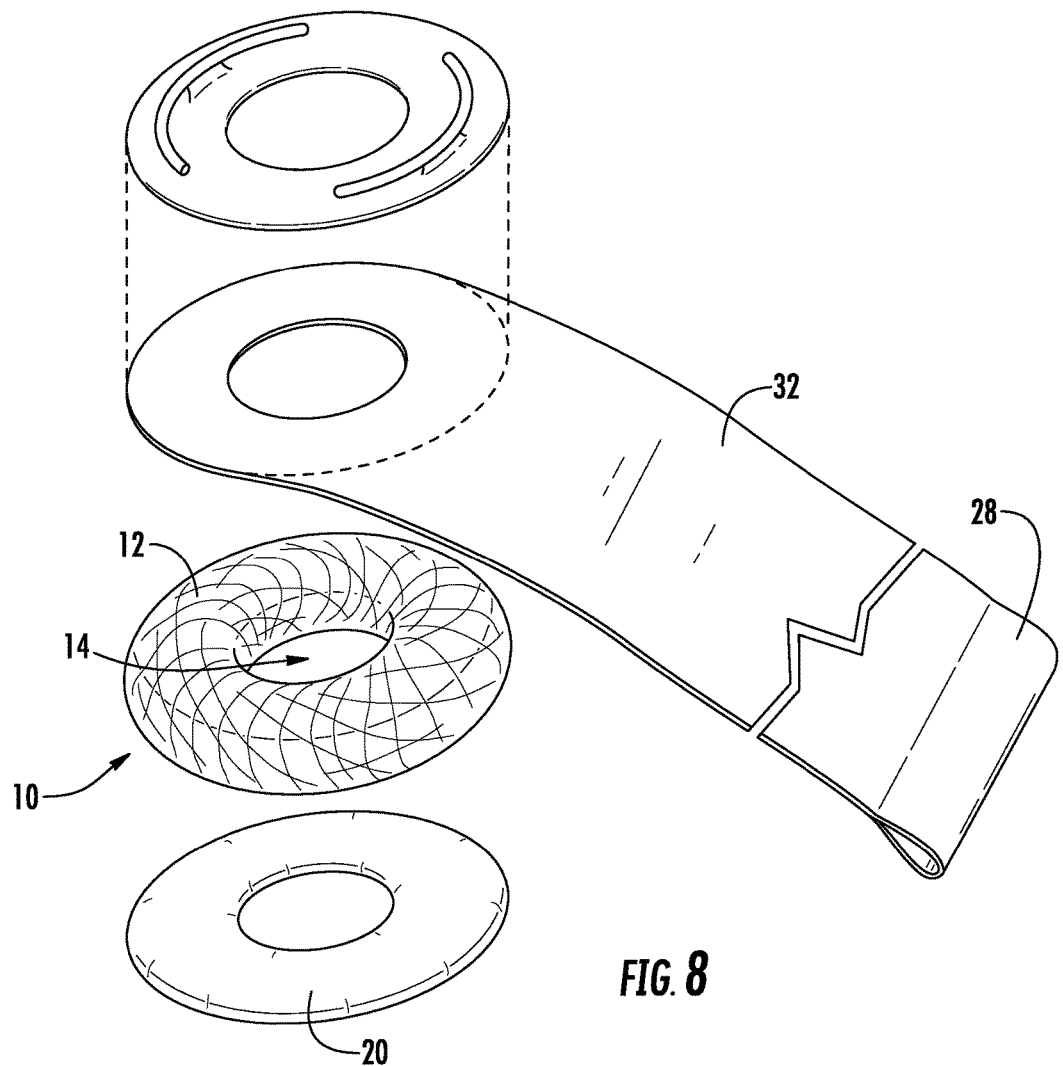
FIG. 8 is a perspective view of the ring compression bandage depicted in FIG. 1, illustrating, in particular, the addition, in a non-expanded view, of a non-adhesive layer to one side of the ring compression bandage, and a cleat plate with holders coupled to an elastic bandage on one end only for use with the ring compression bandage, according to an embodiment of the technology described herein.
Figure 9:
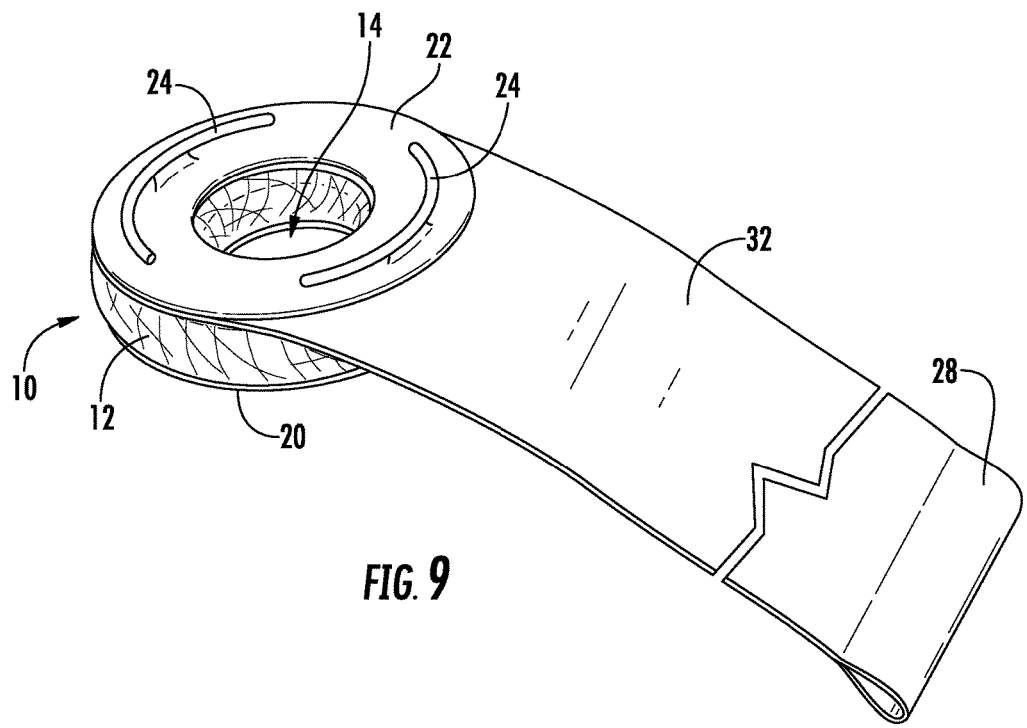
FIG. 9 is a perspective view of the ring compression bandage depicted in FIG. 1, illustrating, in particular, the addition, in a non-expanded view, of a non-adhesive layer to one side of the ring compression bandage, and a cleat plate with holders coupled to an elastic bandage on one end only for use with the ring compression bandage, according to an embodiment of the technology described herein.
Figure 10:
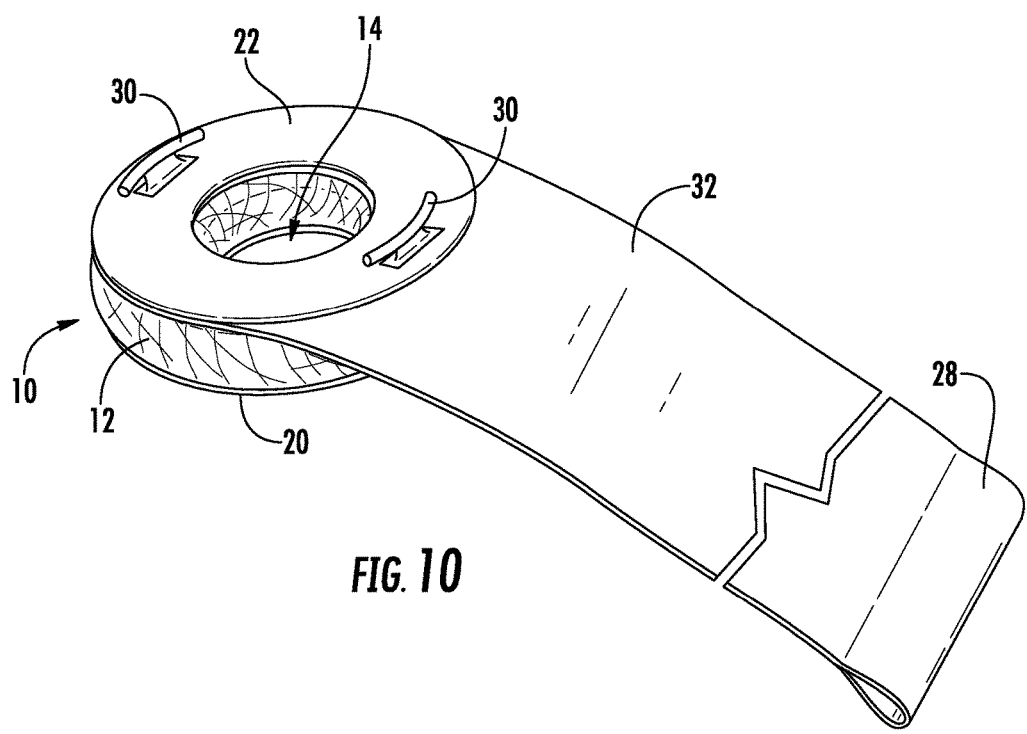
FIG. 10 is a perspective view of the ring compression bandage depicted in FIG. 1, illustrating, in particular, the addition, in a non-expanded view, of a non-adhesive layer to one side of the ring compression bandage, and a cleat plate with alternative cleat holders coupled to an elastic bandage on one end only for use with the ring compression bandage, according to an embodiment of the technology described herein.
Figure 18:
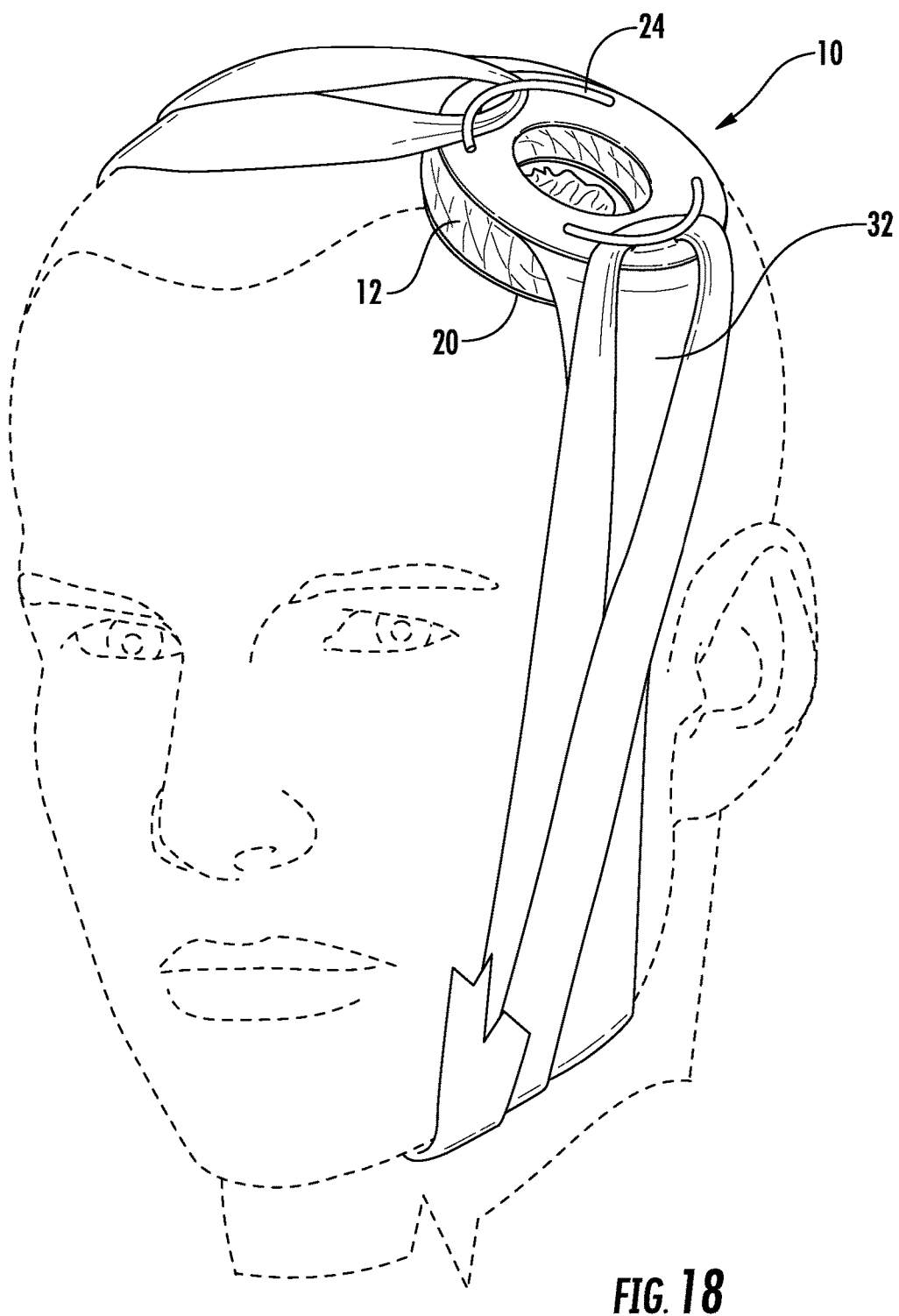
FIG. 18 is a perspective view of the ring compression bandage depicted in use for a person having a traumatic head injury, illustrating, in particular, the ring compression bandage having an elastic bandage attached at one end only and configured for wrap around head and under chin of the patient are around the cleats, according to an embodiment of the technology described herein.
Figure 19:
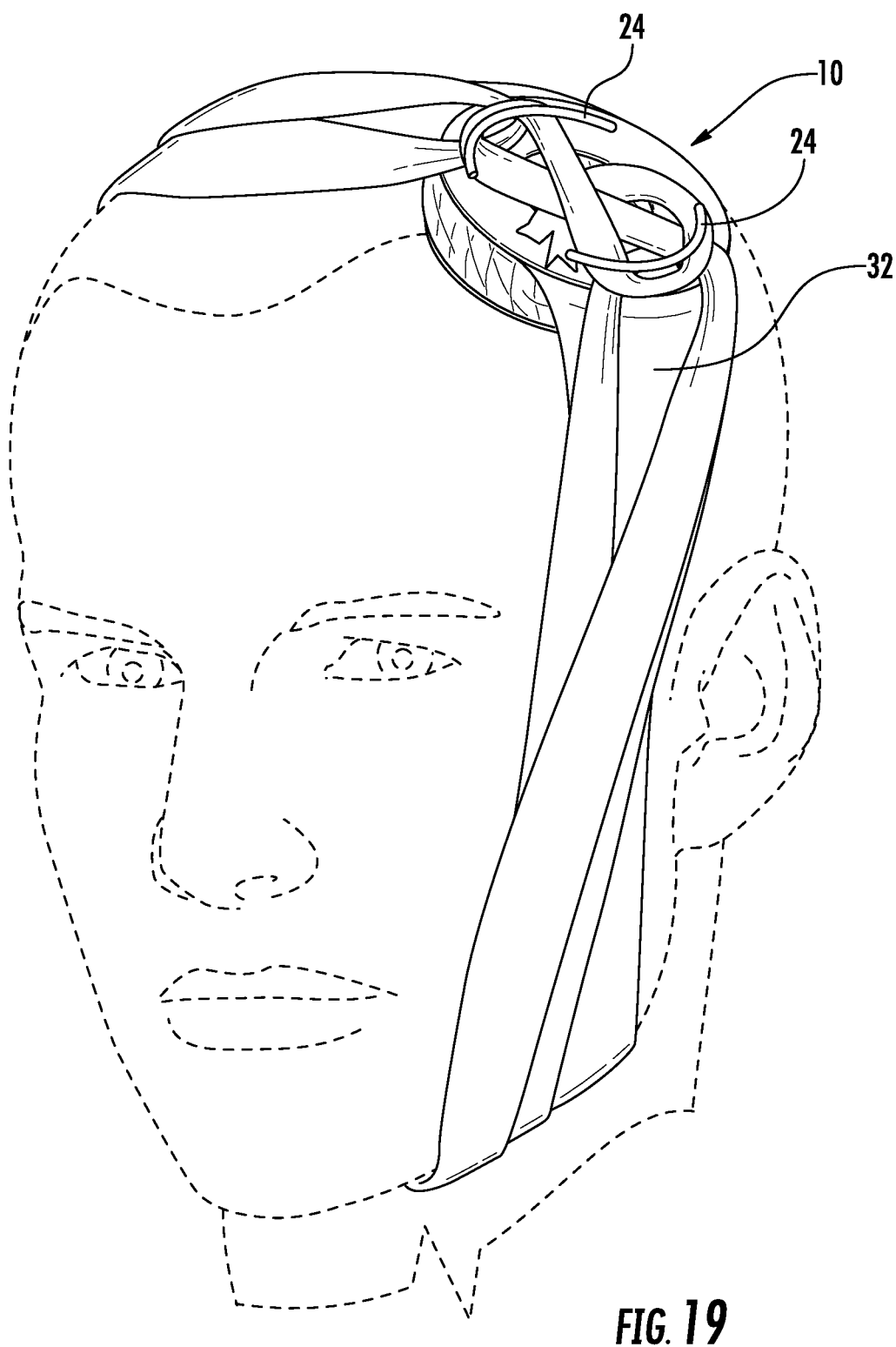
FIG. 19 is a perspective view of the ring compression bandage depicted in FIG. 18 and use for a person having a traumatic head injury, illustrating, in particular, further wrapping steps, according to an embodiment of the technology described herein.

In at least one embodiment, the toroidal compression bandage 10 further includes an attached supplemental fabric 32 coupled to a top surface of the toroidal compression bandage 10 and extended on at least one end in one direction from the toroidal compression bandage. This configuration is depicted in FIGS. 8, 9, 10 and is further shown in use in FIGS. 18 and 19. This configuration provides a means to wrap securely the toroidal compression bandage upon a wound area. The attached supplemental fabric 32 includes loop 28 in at least one embodiment. Loop 28 is useful in securing the attached supplemental fabric 32 to a cleat, discussed below.

Figure 5:
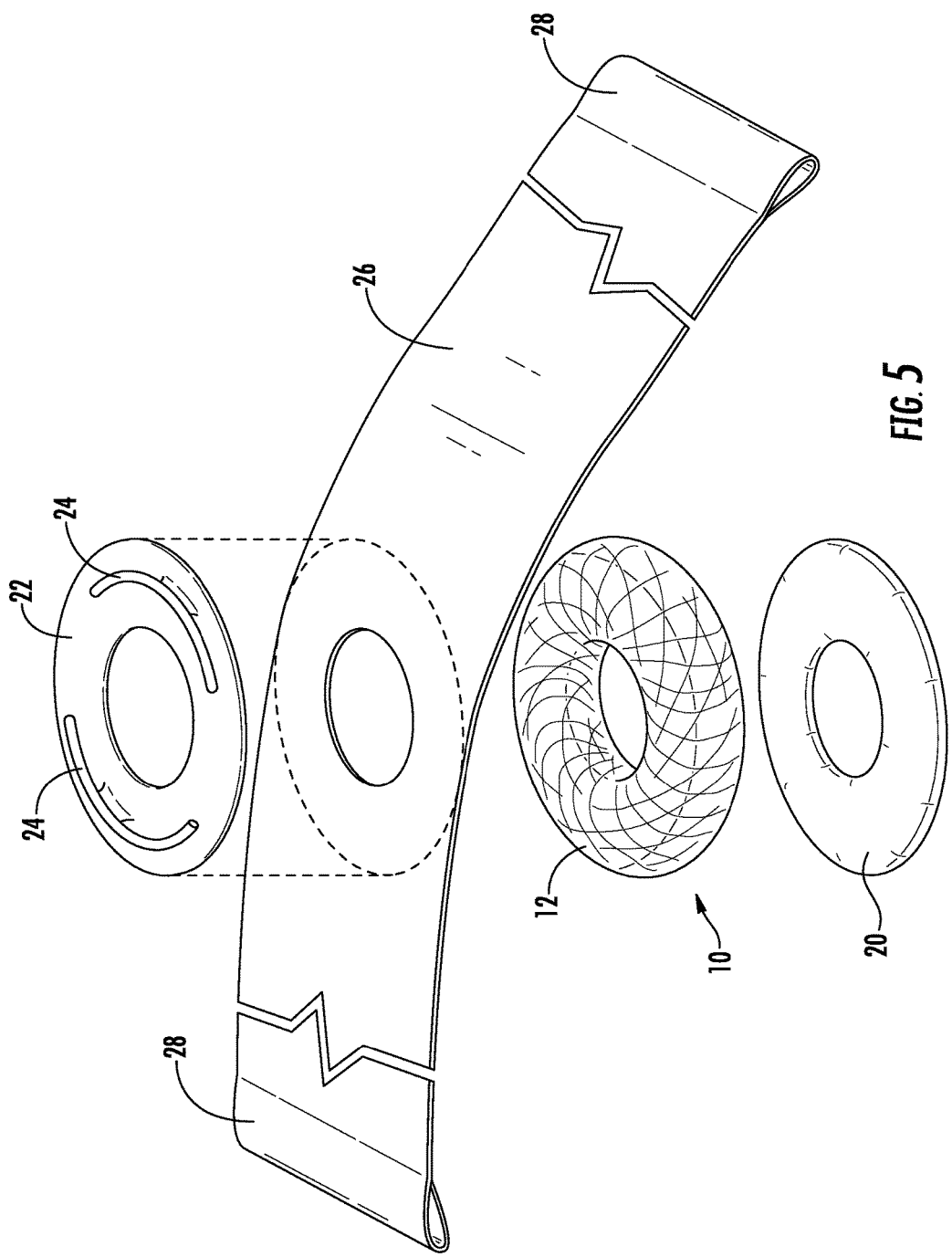
FIG. 5 is a perspective view of the ring compression bandage depicted in FIG. 1, illustrating, in particular, the addition, in an expanded view, of a non-adhesive layer to one side of the ring compression bandage, and a cleat plate with holders coupled to an elastic bandage for use with the ring compression bandage, according to an embodiment of the technology described herein.
Figure 6:
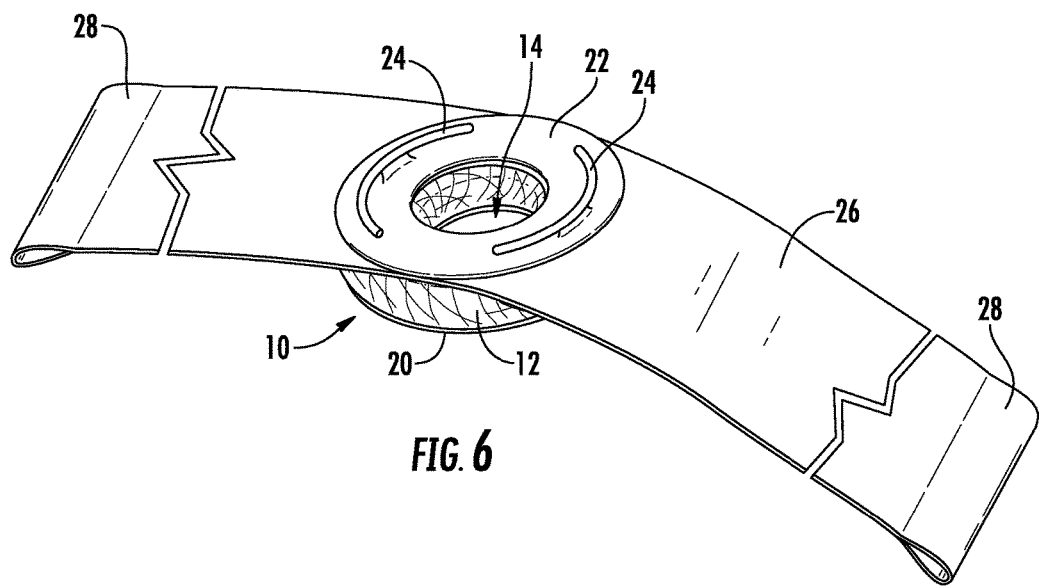
FIG. 6 is a perspective view of the ring compression bandage depicted in FIG. 1, illustrating, in particular, the addition, in a non-expanded view, of a non-adhesive layer to one side of the ring compression bandage, and a cleat plate with holders coupled to an elastic bandage for use with the ring compression bandage, according to an embodiment of the technology described herein.
Figure 7:
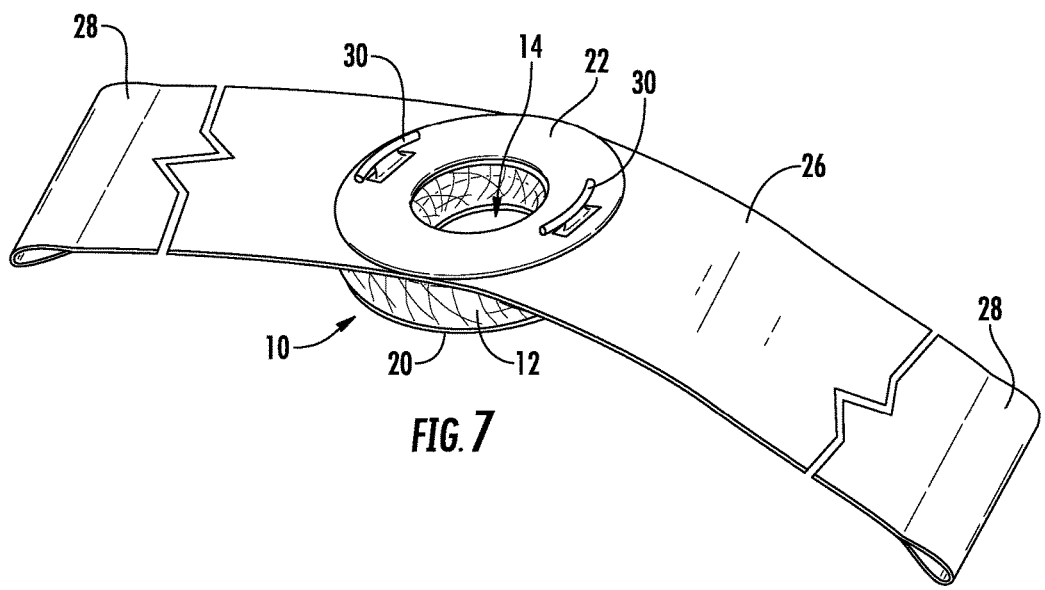
FIG. 7 is a perspective view of the ring compression bandage depicted in FIG. 1, illustrating, in particular, the addition, in a non-expanded view, of a non-adhesive layer to one side of the ring compression bandage, and a cleat plate with alternative cleat holders coupled to an elastic bandage for use with the ring compression bandage, according to an embodiment of the technology described herein.

In at least one embodiment, the toroidal compression bandage 10 further includes an attached supplemental fabric 26 coupled to a top surface of the toroidal compression bandage 10 and extended in two opposed directions on opposing ends of the toroidal compression bandage. This configuration is depicted in FIG. 5 and is further shown in use in FIGS. 16 and 17. This configuration provides a means to wrap securely the toroidal compression bandage 10 upon a wound area. The attached supplemental fabric 26 includes loop 28 at each end in at least one embodiment. Loops 28 are useful in securing the attached supplemental fabric 26 to the cleats, discussed below.

Figure 20:
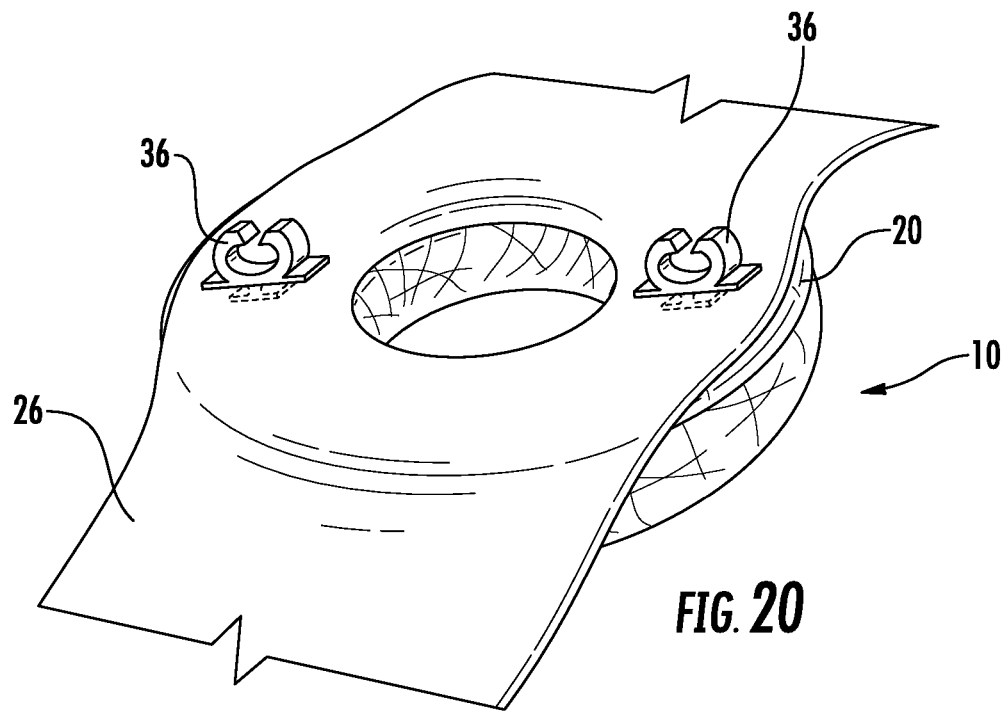
FIG. 20 is a perspective view of the ring compression bandage having alternative cleats and an attached elastic bandage, according to an embodiment of the technology described herein.

In at least one embodiment, the toroidal compression bandage further includes a cleat plate 22. The cleat plate 22 is disposed upon a top surface of the toroidal compression bandage 10. The cleat plate 22 includes at least one cleat 24 disposed upon the cleat plate 22 and configured to receive an attached supplemental fabric or an unattached supplemental fabric to wrap securely the toroidal compression bandage 10 upon a wound area. Alternative cleats 30 are depicted in FIG. 10. Alternatives cleats 36 are depicted in FIG. 20, with attached supplemental fabric 26 and 21, with supplement unattached fabric 34.

In at least one embodiment, the pair of cleats 24 is disposed upon the cleat plate 22 parallel to a direction of the attached supplemental fabric or an unattached supplemental fabric.

In at least one embodiment, the pair of cleats 24 is disposed upon the cleat plate 22 perpendicular to a direction of the attached supplemental fabric or an unattached supplemental fabric.

Figure 21:
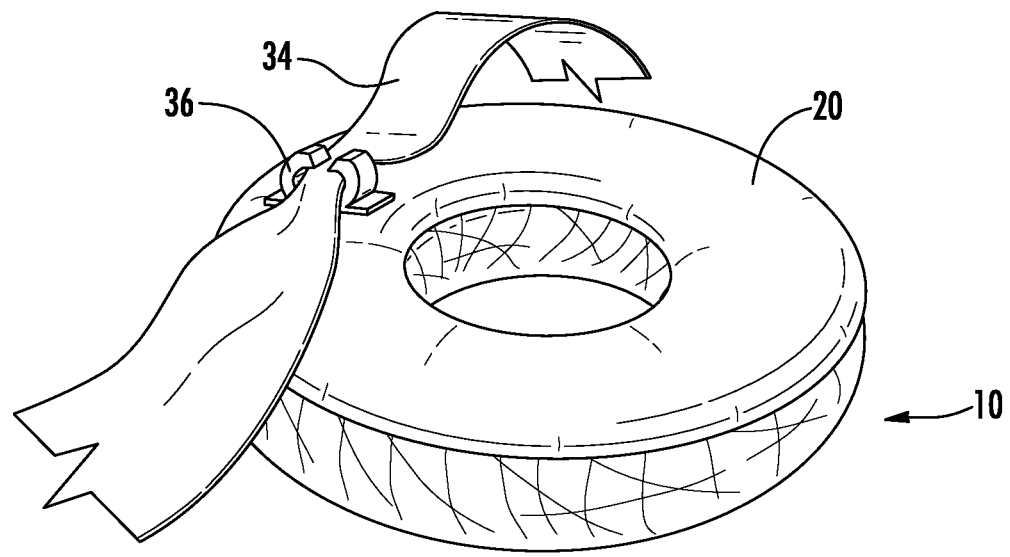
FIG. 21 is a perspective view of the ring compression bandage having alternative cleats and a supplemental, non-attached elastic bandage, according to an embodiment of the technology described herein.

In at least one embodiment, the toroidal compression bandage 10 further includes an unattached supplemental fabric 34 to provide a means to wrap securely the toroidal compression bandage around an object. An unattached supplemental fabric 34 is depicted in FIG. 21.

The toroidal compression bandage 10 can be manufactured by utilizing a weaved nylon (or similar material) tube 18 and stuffing the nylon tube with cotton so that the tube is firm and resists compression. The cotton-stuffed nylon-tube is then wrapped with several layers of gauze material.

Optionally, once wrapping the gauze is completed, attach a stick-resistant bandage material to one side of the ring shaped article. The stick-resistant bandage material may be glued or sewn into the gauze, or sewn to a supplemental fabric. The supplemental fabric is attached as the outer layer of the ring compression bandage.

Optionally, and with or without inclusion of the first option above, a stick-resistant material is attached to the top of the ring that covers the opening to prevent debris from entering the exposed cavity. This embodiment is useful in such cases as a head wound with exposed brain matter in an environment with foreign matter, such as woods, desert, or battlefield conditions, especially when the bandage would be attached to the wound with a non-stick resistant bandage such as an elastic bandage, a fabric bandana, or non-sterile torn fabric. The stick-resistant cover should be removable or easily tear-able so that the bandage could be altered to use for a penetration wound with exposed foreign article (such as pen, nail, long splinter, or shrapnel).

Optionally, and with or without inclusion of the first and second options above, supplemental fabric is attached to two opposite edges of the ring in order to attach the ring to the body. This prevents the necessity of using a supplemental bandage material such as a roll of gauze bandage or elastic bandage or non-sterile torn fabric when applying the ring to the injury.

Optionally, the cotton stuffed nylon tube is a single pressure resistant round foam tube on which the gauze is wrapped around in at least one embodiment. The foam tube is a much-cheaper construction and will not provide the additional blood absorbency that a the cotton stuffed nylon tube would provide, however, it would provide the primary beneficial features of being a pre-fabricated, ring shaped bandage that will facilitate pressure applied to an open head wound or protruding object wound.

In use the toroidal compression bandage 10 is ideally suited for two different injuries: (1) a head injury where the skull is compromised and brain matter is exposed, and (2) a long-shaped foreign object (such as a pen, nail, splinter, or shrapnel) penetrates the body or extremity and a significant portion of that object remains outside of the body.

Figure 16:
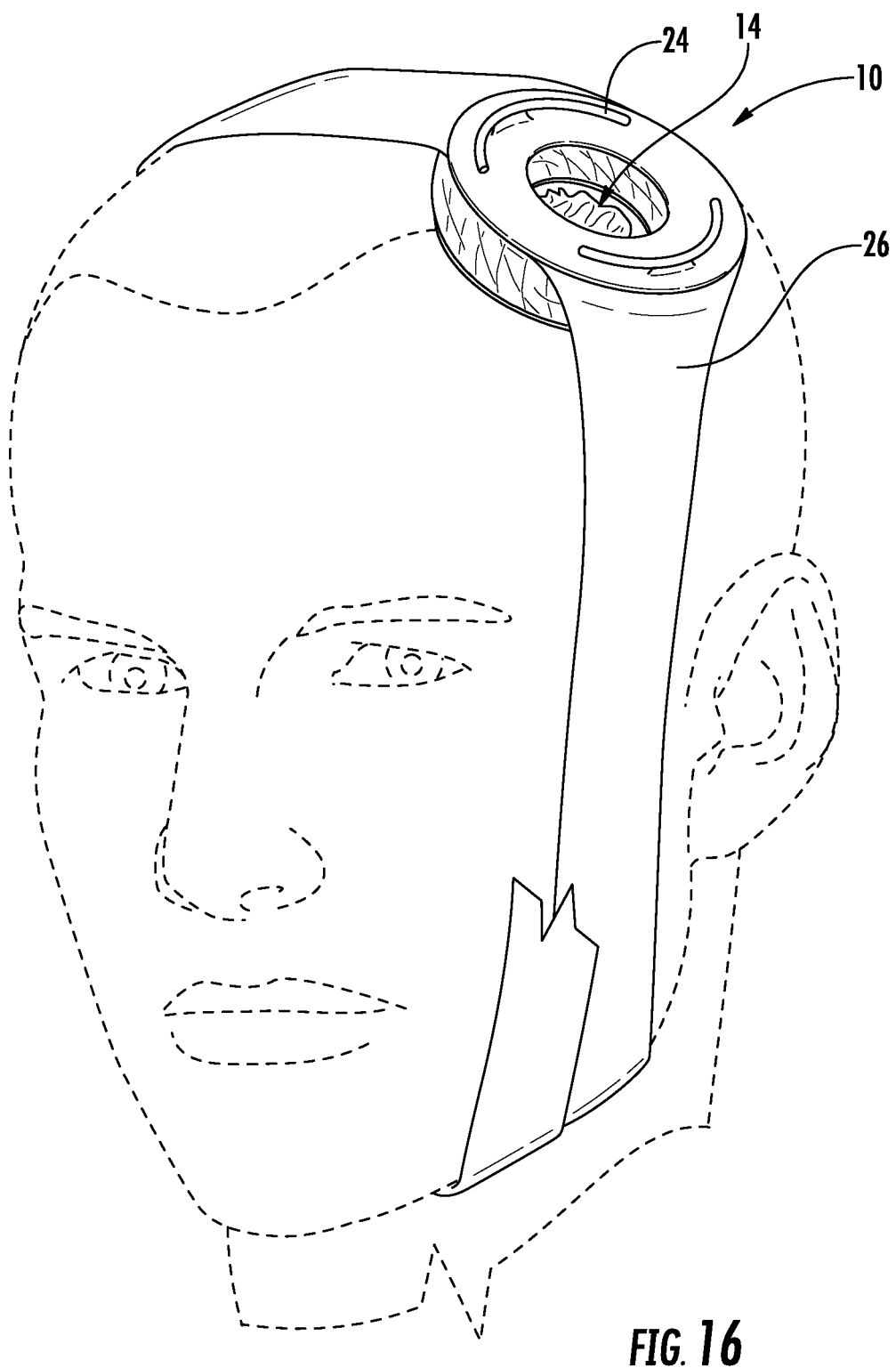
FIG. 16 is a perspective view of the ring compression bandage depicted in use for a person having a traumatic head injury, illustrating, in particular, the ring compression bandage having an elastic bandage attached at each end and configured for wrap around head and under chin of the patient are around the cleats, according to an embodiment of the technology described herein.
Figure 17:
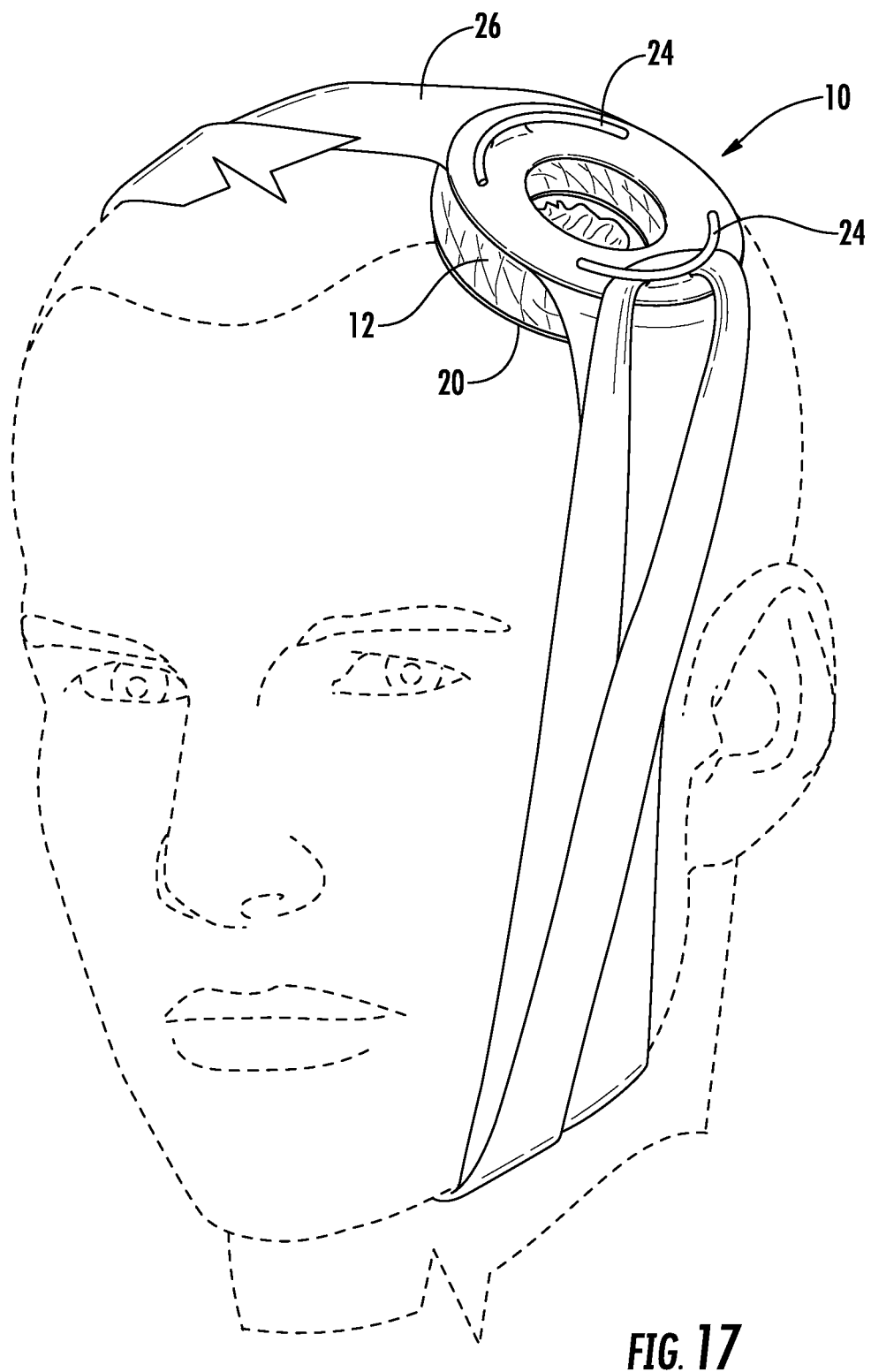
FIG. 17 is a perspective view of the ring compression bandage depicted in FIG. 16 and use for a person having a traumatic head injury, illustrating, in particular, further wrapping steps, according to an embodiment of the technology described herein.

In the case of a head injury where brain matter is exposed, a conventional bandage should not be used because at the location where the bandage comes into contact with brain matter, the bandage may cause additional, significant brain injury. The toroidal compression bandage 10, with an appropriate diameter, would be applied to the area around the exposed injury and attached using an appropriate fabric (gauze, elastic bandage, torn fabric, and so forth) so that consistent pressure is applied around the injury to facilitate reducing the bleeding until appropriate medical care can be administered. As depicted in FIG. 16, for example, the injured area of the head/brain is not directly touched by the toroidal compression bandage 10 because of aperture 14.

The problem of how to apply pressure to an injury with compromised skull and exposed brain matter, in order to reduce bleeding at the area of the injury and not contact the exposed brain matter is normally solved using a triangle bandage wound into a circle and placed around the injured area, then attached using rolled gauge bandage strip or elastic bandage. The problems with this method are: 1) the time it takes to convert a triangle bandage into a ring bandage; 2) knowledge of how to make the triangle-ring bandage is required by the responder providing the care; 3) lack of absorbency of the triangle material; and 4) inconsistency of compression around the triangle-ring due to inconsistent resistance provided by the triangle-ring due to the hand-made characteristic of the article.

The toroidal compression bandage 10 as described in this disclosure is professionally prefabricated. So the time required to make the bandage is only the time required to remove it from the responder's kit and open the packaging. Being prefabricated requires no knowledge by the responder in order to produce the article. Further, the gauze material surrounding the firm core of the ring compression bandage provides absorbency for blood leaking from the injury than a traditional triangle bandage would. Finally, the core of the ring compression bandage will provide firm, consistent pressure against the body or extremity in order to best reduce blood flow into the injured area, superior to the inconsistent resistance of the hand-made ring-wound triangle bandage.

Figure 14:
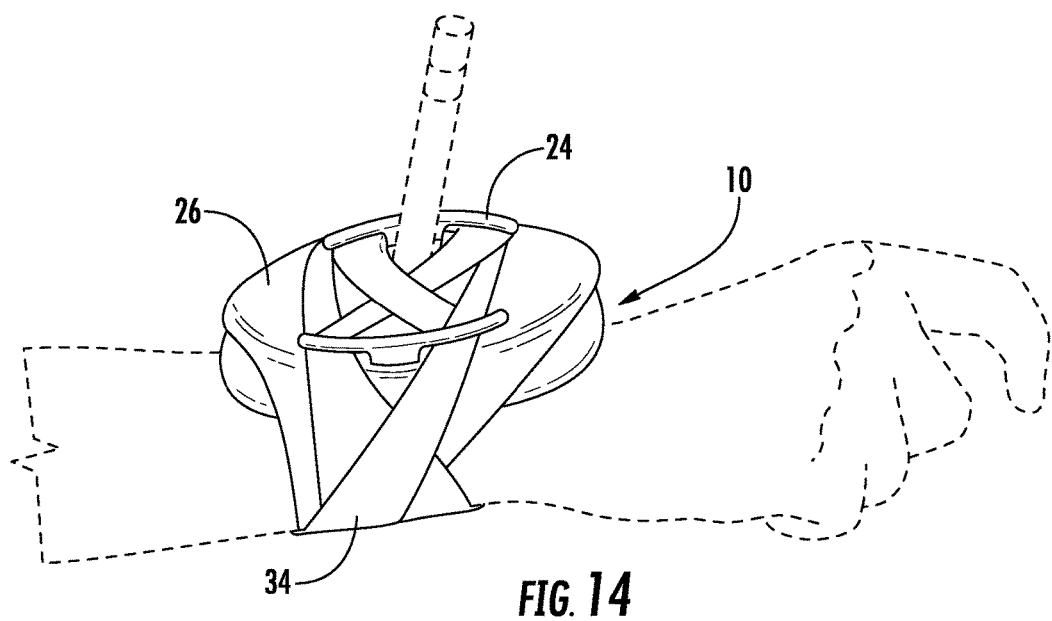
FIG. 14 is a perspective view of the ring compression bandage depicted in use for a person having a traumatic puncture-type wound to an extremity, illustrating, in particular, the ring compression bandage having cleats and a an attached bandage and further using a separate bandage to wrap the ring compression bandage, according to an embodiment of the technology described herein.
Figure 15:
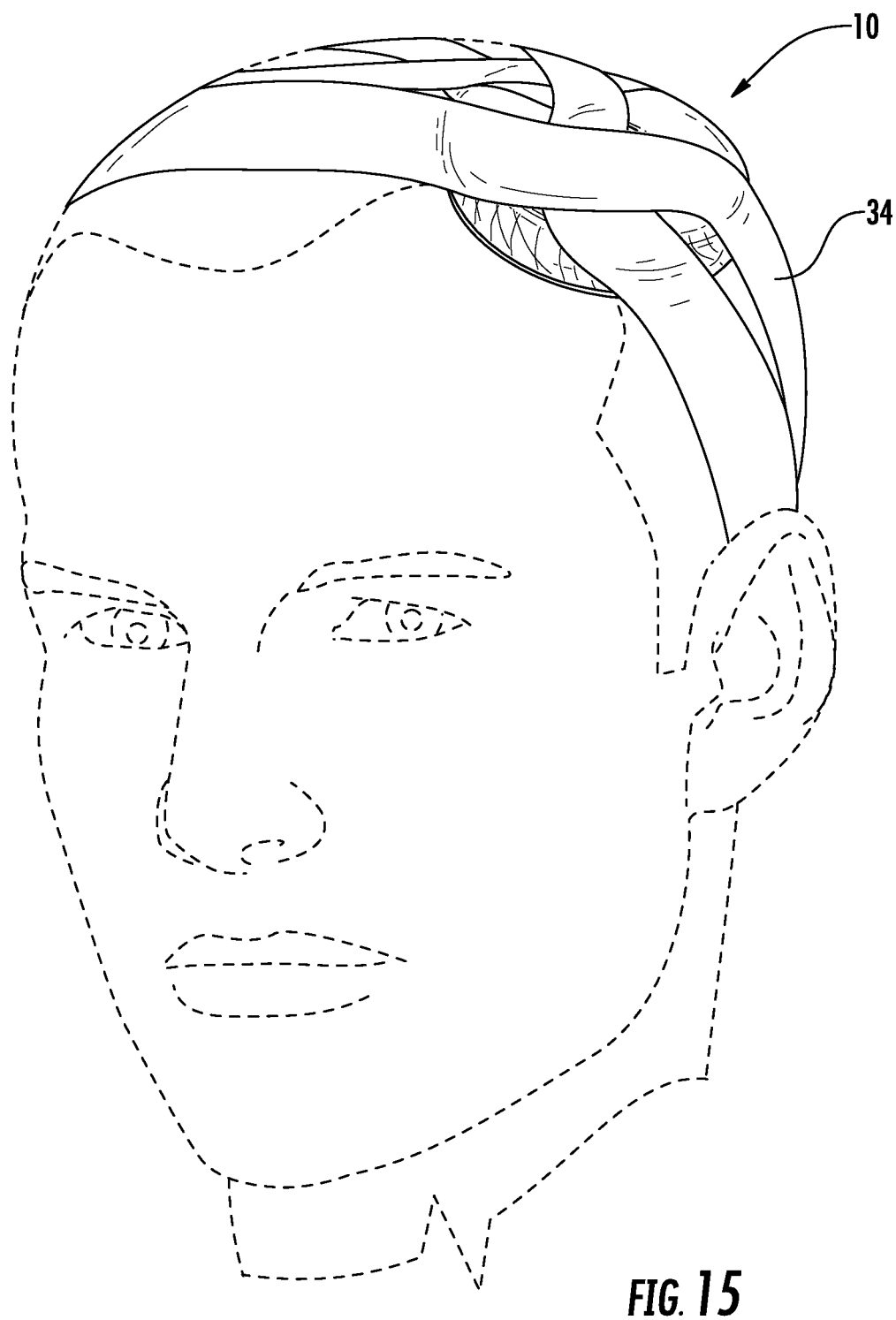
FIG. 15 is a perspective view of the ring compression bandage depicted in use for a person having a traumatic head injury, illustrating, in particular, the ring compression bandage and using a separate bandage to wrap the ring compression bandage, according to an embodiment of the technology described herein.

In the case of a protrusion injury, the application of a bandage should be around the protrusion so as to not rub against the protruding foreign object because movement of that object will cause additional trauma to the injury. The toroidal compression bandage 10 is placed around the protrusion with ample space to prevent the bandage from causing additional trauma and attached to the body or extremity using an appropriate fabric so that consistent pressure is applied around the injury to facilitate reducing the bleeding until appropriate medical care can be administered. As depicted in FIG. 14, for example, the protrusion exits aperture 14 of the toroidal compression bandage 10.

The problem of how to apply pressure to an injury of a foreign object protruding from the body or an extremity is normally resolved by applying a gauze bandage strip (from a rolled gauze bandage) or an elastic bandage around the protruding object with as much pressure as possible without the bandage coming into contact with the protrusion, or alternatively placing tape on two opposite sides of the protrusion and the body to reduce movement of the protrusion and then wrapping the bandage around the body or extremity and close to or touching the protrusion so that equal pressure to both sides of the protrusion to minimize the movement of the protruding object. The problem with the first method is that there is reduced pressure on around the injury in order to prevent the bandage from coming into contact with the protrusion. The problem with the second method is that with contact of the bandage to the protrusion, the protruding object will move, if only a little. The little movement may cause little or severe additional trauma depending on the characteristics of the foreign object and the organic parts the object is in contact with below the skin. The responder providing care is unlikely to evaluate or mitigate this circumstance at the point of first-aid. The toroidal compression bandage 10 described in this disclosure provides ample space from the point of injury to mitigate the probability that the bandage will cause additional trauma to the point of injury. Additionally, because of the consistent firm core 18 of the toroidal compression bandage 10 a tighter seal (that is more compression) can be applied to the body or extremity in order to reduce blood flow, better than the application of conventional rolled bandages applied around the area of injury.

Although this technology has been illustrated and described herein with reference to preferred embodiments and specific examples thereof, it will be readily apparent to those of ordinary skill in the art that other embodiments and examples can perform similar functions and/or achieve like results. All such equivalent embodiments and examples are within the spirit and scope of the invention and are intended to be covered by the following claims.

What is claimed is:

1. A toroidal compression bandage comprising:
   a tubular, circular core, the core comprised of a material to resist compression and to reduce blood flow into an injured area;
   a sterile fibrous material, defined by an absorbency of a predetermined amount;
   a torus ring compression bandage form comprised of the fibrous absorbent material in a rolled, wrapped tubular form, around the tubular, circular core, and of a tubular, circular shape defined by a circle revolved in three-dimensional space about a circular axis coplanar with the circle, wherein the axis of revolution does not touch the rotated circle, thereby to define a torus ring compression bandage for placement around a trauma wound to avoid direct contact of the trauma wound, and for absorption placement around the trauma wound;
   an aperture defined within a center area of the torus ring compression bandage as it is formed, the aperture having a predetermined diameter and configured for placement directly over a trauma wound to avoid direct contact with the trauma wound, wherein the torus ring compression bandage is configured for placement circumferentially around the trauma wound and the aperture provides that no direct contact of the torus ring compression bandage is made to the trauma wound and for absorption placement circumferentially around the trauma wound; and
   a compression surface defined on an underside of the torus ring compression bandage, the compression surface configured for circumferential placement on a surface around the trauma wound to avoid direct contact of the trauma wound, and for absorption placement around the trauma wound.

2. The toroidal compression bandage of claim 1, further comprising:
   an outer encasement defined in a torus ring shape as the torus ring compression bandage and configured to surround and encase the torus ring compression bandage and to contain the fibrous material and compression bandage form.

3. The toroidal compression bandage of claim 2, wherein the outer encasement comprises cotton netting.

4. The toroidal compression bandage of claim 1, wherein the fibrous material, defined by an absorbency of a predetermined amount comprises gauze.

5. The toroidal compression bandage of claim 1, wherein the fibrous material, defined by an absorbency of a predetermined amount comprises cotton.

6. The toroidal compression bandage of claim 1, wherein the compression bandage form comprised of the fibrous absorbent material in a rolled, wrapped form is rolled, wrapped around the core of tubular shape.

7. The toroidal compression bandage of claim 6, wherein the core of tubular shape is hollow and the toroidal compression bandage further comprises supplemental fibrous material disposed within the hollow core of tubular shape.

8. The toroidal compression bandage of claim 6, wherein the core of tubular shape is solid.

9. The toroidal compression bandage of claim 6, wherein the core of tubular shape is foam.

10. The toroidal compression bandage of claim 6, wherein the core of tubular shape comprises a weaved nylon tube.

11. The toroidal compression bandage of claim 6, wherein the core of tubular shape comprises a porous nylon tube.

12. The toroidal compression bandage of claim 1, further comprising:
    a first non-adhesive pad disposed on an underside surface of the toroidal compression bandage.

13. The toroidal compression bandage of claim 1, further comprising:
    a second non-adhesive pad disposed on a topside surface of the toroidal compression bandage.

14. The toroidal compression bandage of claim 1, further comprising:
    a third non-adhesive pad configured for placement to cover over a topside surface of the toroidal compression bandage and the aperture defined within the center area of the torus ring compression bandage and removable.

15. The toroidal compression bandage of claim 1, further comprising:
    an attached supplemental fabric coupled to a top surface of the toroidal compression bandage and extended on at least one end in one direction from the toroidal compression bandage.

16. The toroidal compression bandage of claim 1, further comprising:
    an attached supplemental fabric coupled to a top surface of the toroidal compression bandage and extended in two opposed directions on opposing ends of the toroidal compression bandage.

17. The toroidal compression bandage of claim 1 further comprising:
    a cleat plate disposed upon a top surface of the toroidal compression bandage; and
    at least one cleat disposed upon the cleat plate and configured to receive an attached supplemental fabric or an unattached supplemental fabric to wrap securely the toroidal compression bandage upon a wound area.

18. The toroidal compression bandage of claim 1 further comprising:
- a cleat plate disposed upon a top surface of the toroidal compression bandage; and
- a pair of cleats disposed upon the cleat plate and configured to receive an attached supplemental fabric or an unattached supplemental fabric to wrap securely the toroidal compression bandage upon a wound area;
- wherein the pair of cleats are disposed upon the cleat plate are parallel to a direction of the attached supplemental fabric or an unattached supplemental fabric.

19. The toroidal compression bandage of claim 1 further comprising:
- a cleat plate disposed upon a top surface of the toroidal compression bandage; and
- a pair of cleats disposed upon the cleat plate and configured to receive an attached supplemental fabric or an unattached supplemental fabric to wrap securely the toroidal compression bandage upon a wound area;
- wherein the pair of cleats are disposed upon the cleat plate are perpendicular to a direction of the attached supplemental fabric or an unattached supplemental fabric.

20. The toroidal compression bandage of claim 1, further comprising:
- an unattached supplemental fabric wherein a configuration of a combined attached supplemental fabric provides a means to wrap securely the toroidal compression bandage around an object.

* * * * *